United States Patent
Sullivan

(10) Patent No.: US 9,566,440 B2
(45) Date of Patent: Feb. 14, 2017

(54) BALANCED CHARGE WAVEFORM FOR TRANSCUTANEOUS PACING

(75) Inventor: Joseph L. Sullivan, Kirkland, WA (US)

(73) Assignee: Physio-Control, Inc., Redmond, WA (US)

( * ) Notice: Subject to any disclaimer, the term of this patent is extended or adjusted under 35 U.S.C. 154(b) by 711 days.

(21) Appl. No.: 13/225,181

(22) Filed: Sep. 2, 2011

(65) Prior Publication Data

US 2011/0319950 A1    Dec. 29, 2011

Related U.S. Application Data

(62) Division of application No. 10/396,023, filed on Mar. 24, 2003, now Pat. No. 8,027,721.

(51) Int. Cl.
*A61N 1/362* (2006.01)

(52) U.S. Cl.
CPC .................................. *A61N 1/3625* (2013.01)

(58) Field of Classification Search
USPC ......... 607/1–2, 7, 10, 13, 27, 63, 68, 70, 74
See application file for complete search history.

(56) References Cited

U.S. PATENT DOCUMENTS

| | | | |
|---|---|---|---|
| 4,821,723 A | 4/1989 | Baker, Jr. et al. | |
| 5,083,562 A | 1/1992 | de Coriolis et al. | |
| 5,205,284 A | 4/1993 | Freeman | |
| 5,456,710 A | 10/1995 | Gadsby | |
| 5,601,608 A | 2/1997 | Mouchawar | |
| 5,782,882 A | 7/1998 | Lerman et al. | |
| 5,871,506 A | 2/1999 | Mower | |
| 5,964,787 A | 10/1999 | Kerver et al. | |
| 6,067,470 A | 5/2000 | Mower | |
| 6,136,019 A | 10/2000 | Mower | |
| 6,141,586 A | 10/2000 | Mower | |
| 6,141,587 A | 10/2000 | Mower | |
| 6,178,351 B1 | 1/2001 | Mower | |
| 6,256,534 B1 | 7/2001 | Dahl | |
| 6,295,470 B1 | 9/2001 | Mower | |
| 6,332,096 B1 | 12/2001 | Mower | |
| 6,337,995 B1 | 1/2002 | Mower | |
| 6,341,235 B1 | 1/2002 | Mower | |
| 6,343,232 B1 | 1/2002 | Mower | |
| 6,411,845 B1 | 6/2002 | Mower | |
| 6,411,847 B1 | 6/2002 | Mower | |
| 6,487,448 B2 | 11/2002 | Sullivan et al. | |
| 6,505,079 B1 | 1/2003 | Foster et al. | |
| RE38,119 E | 5/2003 | Mower | |
| 6,697,670 B2 | 2/2004 | Chomenky et al. | |
| 6,751,501 B1 | 6/2004 | Schuler et al. | |
| 6,980,856 B2 | 12/2005 | Sullivan et al. | |

*Primary Examiner* — Deborah Malamud
(74) *Attorney, Agent, or Firm* — Lane Powell PC

(57) ABSTRACT

External pacemaker systems and methods deliver pacing waveforms that minimize hydrolysis of the electrode gel. Compensating pulses are interleaved with the pacing pulses, with a polarity and duration that balance the net charge at the electrode locations. The compensating pulses are preferably rectangular for continuous pacing, and decay individually for on-demand pacing.

2 Claims, 3 Drawing Sheets

US 9,566,440 B2

BALANCED CHARGE WAVEFORM FOR TRANSCUTANEOUS PACING

CROSS-REFERENCE TO RELATED APPLICATIONS

This application is a division of U.S. patent application Ser. No. 10/396,023 entitled "BALANCED CHARGE WAVEFORM FOR TRANSCUTANEOUS PACING" filed Mar. 24, 2003, and issued as U.S. Pat. No. 8,027,721 on Sep. 27, 2011.

TECHNICAL FIELD

The present invention relates generally to medical pacemaker systems, and more particularly to devices and methods that generate pacing waveforms for minimizing patient skin burns during long-term transcutaneous defibrillation.

BACKGROUND

Systems are made for administering to patients pacing pulses externally. Advantageously, external defibrillators may also administer such external pacing. A common electrode used to connect a heart pacer to a patient incorporates an electrically conductive, impedance-decreasing gel disposed between a flexible conductive plate and the patient's skin. The gel ensures good electrical contact between the patient and the conductive plate, and adheres the electrode to the patient's skin. During pacing, pulses are generated by the heart pacer and applied through the electrodes and into the patient. Typical pacing equipment will commonly deliver a pacing pulse having an amplitude of up to 300 volts, and a maximum current of about 0.2 amps. Such a pacing pulse may be applied to a patient up to 170 times a minute, for periods as long as 24 hours.

FIG. 1 is a diagram of a pacing waveform 10 currently used for the transcutaneous pacing of a patient. Pacing waveform 10 is shown on a graph having a horizontal axis of time, and a vertical axis of current (in milliamps) applied to the patient. Prior art pacing waveform 10 comprises a positive stimulating pacing pulse 12 having an amplitude 14 and a duration t1. After application of the positive stimulating pulse, the amplitude of the waveform falls to at or near 0 for duration t2. The period between application of the positive stimulating pulses is the sum of duration t1 and t2.

Application of pacing waveform 10 generates an excess of positive charge flowing through the electrodes. The excess charge causes hydrolysis of the electrode gel, producing hydrogen and oxygen between the electrode and the patient's skin. During long-term transcutaneous pacing, the generation of hydrogen and oxygen causes the electrode impedance to increase and the electrode pH to change.

A problem arises when such transcutaneous pacing is long-term. The changes of an electrode's impedance and pH are dramatic. The hydrogen and oxygen gas, which tend to accumulate between the patient's skin and the flexible conductive plate, and produces two primary undesirable effects. First, the accumulation of the gases generally decreases the conductivity between the electrode and the patient. As the impedance of the electrodes increases, the pacer is forced to compensate by applying a higher voltage to produce a suitable pacing current. Generally, the impedance of the electrodes may reach such a high value that the pacer is unable to generate a sufficient voltage to apply a pacing pulse. At this point, many pacers may stop pacing, and instead generate a "leads off" alarm, on the erroneous determination that the high resistance is caused by one of the electrodes having fallen off the patient.

Second, the gas has a tendency to accumulate in pockets, causing the current density in areas of the electrode to increase. The bubbles tend to insulate the conductive plate from the patient, reducing the surface area of the electrode in contact with the patient. If the density of current flow increases in the areas remaining in contact with the patient, patient discomfort may result. If the current density increases even further, burning of the patient's skin may result. The increasing current density problem is exacerbated with electrodes designed for pediatric use. Pediatric electrodes tend to be smaller and have a smaller conductive surface, yet have current flows comparable to electrodes used for adults.

As hydrolysis occurs during long-term pacing, the pH of the electrode also has a tendency to change. The formation of hydrogen and oxygen bubbles within the electrode cause the gel of one electrode to become more acidic, and the gel of the other electrode to become more basic. For children or patients with sensitive skin, the change in electrode pH can become highly irritating to the dermic layer.

One approach to minimizing the buildup of hydrogen and oxygen gas has been to construct the electrodes in a manner that minimizes the amount of gas that may accumulate. For example, U.S. Pat. No. 5,456,710 entitled 'VENTED ELECTRODE" discloses an electrode construction that allows hydrogen and oxygen buildup within an electrode to pass through a gas-permeable layer and escape from beneath the electrode. The gas generated by hydrolysis can therefore vent to the environment before accumulating and causing the impedance or pH of the electrode to change.

While the accumulation of hydrogen and oxygen in the electrodes may be prevented by appropriately constructing the electrodes, such a solution is only applicable in limited circumstances. The majority of pacing performed today uses traditional, non-vented conducting pads. For those situations where non-vented electrodes are being used, it would be advantageous to find an alternative technique to minimize the hydrolysis of the electrode gel such that the impedance and pH of the electrodes would remain relatively constant over an extended period of time.

BRIEF SUMMARY

The invention overcomes the problem of the prior art. The invention provides external pacemaker systems and methods that deliver pacing waveforms that alleviate the problem of the prior art, by minimizing the hydrolysis of the electrode gel, and thus prevent the resulting harmful effects.

The invention delivers a series of pacing pulses to provide pacing to the patient. In addition, the invention applies a series of compensating pulses interleaved with the pacing pulses. The compensating pulses having a polarity opposite to a polarity of the pacing pulses, to substantially compensate for a long-term charge of the pacing pulses.

Accordingly, the invention generates pacing waveforms that maintain a balanced charge in the electrodes. This minimizes the hydrolysis of the electrode gel during long-term transcutaneous pacing. The invention thus allows long-term transcutaneous pacing without fear that the pacing will be stopped due to excessive electrode impedance. In addition, the invention allows the devices, methods, and waveforms of the invention to be applied using conventional electrodes.

BRIEF DESCRIPTION OF THE DRAWINGS

The foregoing and other aspects and attendant advantages of the invention will become more readily appreciated as the same becomes better understood by reference to the following detailed description, when taken in conjunction with the accompanying drawings, wherein.

DETAILED DESCRIPTION

The following detailed description is merely exemplary in nature and is not intended to limit the invention or the application and uses of the invention. Furthermore, there is no intention to be bound by any expressed or implied theory presented in the preceding technical field, background, brief summary or the following detailed description. As has been mentioned, the invention provides external pacemaker systems and methods that deliver charge-balanced pacing waveforms that alleviate the problems arising from the hydrolysis of the electrode gel. The invention is now described in more detail.

Figure 2:
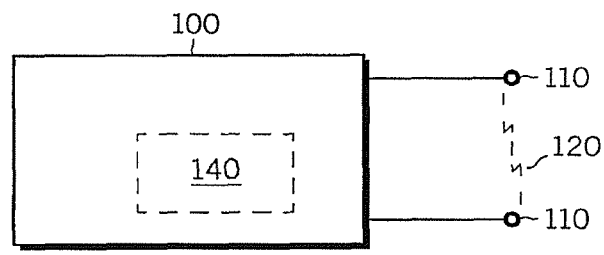
FIG. 2 is a block diagram of a transcutaneous pacing system according to the invention.

FIG. 2 is a block diagram of a transcutaneous pacing system 100 according to the invention. System 100 is made as is known in the art. System 100 may be implemented alone, or in conjunction with other systems, such as defibrillation systems, etc. System 100 may be part of what would be used by trained medical personnel, or untrained users in a home or public access situation, or part of a wearable medical device, etc. System 100 also has transcutaneous pacing electrodes 110 for applying to a patient (not shown). Pulses 120 are delivered to the patient between the applied electrodes 110. In addition, system 100 has a pacing module 140, which generates pacing waveforms for pacing the patient, preferably in the long term. Module 140 may be implemented by electronics, be driven by a processor such as by software programming, digital signal processing, etc. The invention generates an aggregate waveform that includes both pacing pulses and compensating pulses, and applies them as pulses 120 through the pacing electrodes of FIG. 2. Both types may be generated by module 140.

Figure 3:
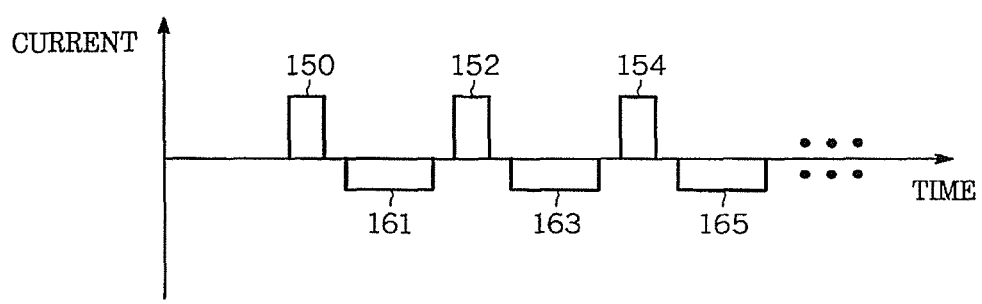
FIG. 3 is a time diagram of a general balanced charge waveform embodiment produced by the device of FIG. 2 and by methods of the invention that is suitable for continuous pacing.

Referring to FIG. 3, a general waveform of the invention is shown. There is a series of pacing pulses (150, 152, 154, . . . ,) to provide pacing to the patient, preferably in the long term. In addition, the invention includes delivering a series of compensating pulses (161, 163, 165, . . . ,) to substantially compensate for a long-term charge of the pacing pulses. To achieve compensation, compensating pulses (161, 163, 165, . . . ,) have a polarity opposite to a polarity of pacing pulses (150, 152, 154, . . . ,). Additionally, as shown in FIG. 3, the amplitude of compensation pulses (161, 163, 165,) is less than the amplitude of pacing pulses (150, 152, 154, . . . ). The two series of pulses are generally interleaved. This means that some of the compensating pulses follow some of the pacing pulses. In the preferred embodiment, they alternate one by one, as shown in FIG. 3. The compensation pulses are shown to be uniform with each other, but that is only for illustration. In fact, they may have different shapes from each other.

As shown in FIG. 3, the general compensating pulses do not necessarily take effect immediately after the pacing pulses. In the preferred embodiment, the compensating pulses start as quickly as possible after the pacing pulses, so as to better reverse the phenomena that are intended to be suppressed. The compensating pulses of the invention have different preferred embodiments for long-term continuous pacing than for on-demand pacing. Indeed, the two scenaria are different.

Figure 4:
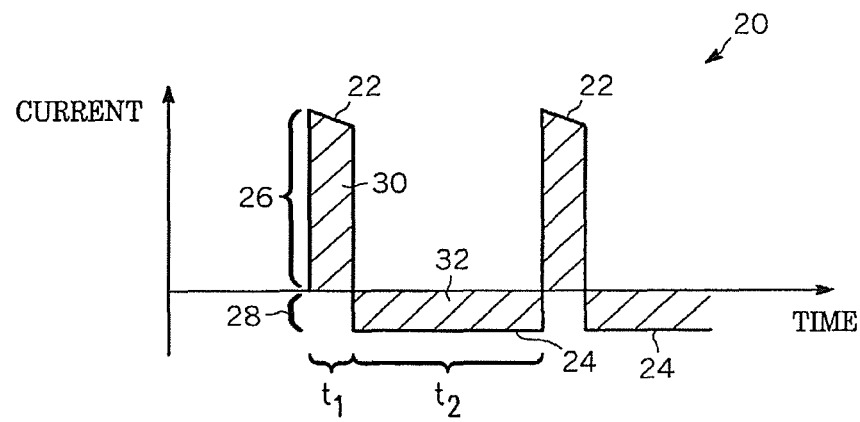
FIG. 4 is a time diagram of an embodiment of the waveform of FIG. 3 that is preferred for continuous pacing.

Referring to FIG. 4, the preferred balanced charge, long-term continuous pacing waveform 20 is shown. One period of balanced charge waveform 20 has a positive stimulating pulse 22 followed by a negative compensating pulse 24. The positive stimulating pulse 22 has an amplitude 26 and a duration t1. The negative compensating pulse 24 has an amplitude 28, and a duration t2. As shown in FIG. 4, the magnitude of amplitude 28 for compensating pulse 24 is less than the magnitude of amplitude 26 for stimulating pulse 22. It will also be observed that the compensating pulses 24 start immediately at an end of a first pacing pulse 22, and last up to an onset of a second pacing pulse 22 that succeeds the first pacing pulse. This presents an advantage that artifacts are avoided. Indeed, it has further been found that any discontinuities in the compensating current pulse will have a tendency to cause artifacts in the monitored electrocardiogram (ECG) during pacing. The artifacts could cause erroneous reading by a clinician monitoring the ECG. In this form, however, a nonzero current will always be applied to a patient over the complete period of the balanced charge waveform. Further, the compensating pulses 24 may have substantially constant current. This reduces the overall instantaneous current applied to the patient from the compensating pulses, as is preferred.

Figure 1:
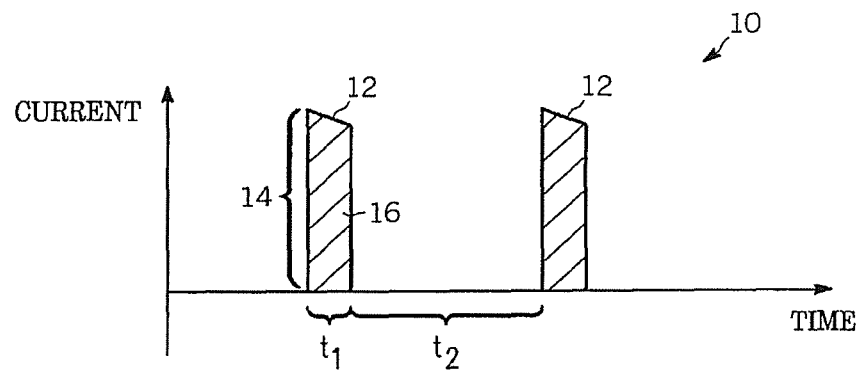
FIG. 1 is a diagram of a prior art pacing waveform generated by a prior art system.

Referring back to FIG. 1, the amount of positive charge applied by the stimulating pulse to the patient is equivalent to the amplitude of the pulse multiplied by the duration of the pulse, represented in FIG. 1 by an area 16 under the pulse. Referring to FIG. 4, in order for the waveform to have a balanced charge, area 30 under the stimulating pulse must be approximately equal to area 32 under the compensating pulse. Having equal areas ensures that the positive charge of the stimulating pulse is balanced by the negative charge of the compensating pulse, and the net current applied to a patient is approximately zero.

During on-demand pacing, however, a pacing pulse for stimulating that patient is generated only when an absence of a patient's heartbeat is detected. Several stimulating pulses may therefore be regularly applied for a period of time, followed by a period when no stimulating pulses are applied. As such, the balance charge waveform 20 shown in FIG. 4 would be ideal for on-demand pacing only if it were guaranteed that the last pacing pulse would be followed by a corresponding compensating pulse, and then the waveform would end. If the pacing pulses discontinued and then the compensating pulses continued indefinitely, the same effect would be accomplished as the prior art problem that the invention solves.

Other waveforms according to the invention are now described, that are better suited for on-demand pacing. In those, a current of the compensating pulses has a waveform of decay from an initially high value. The decay ends in a zero value. In some embodiments, as is preferred, the decay completes to bring the pulse to zero before the next pulse is applied, which ensures that the charge of the waveform remains balanced. In other embodiments the decay may be interrupted by the next pacing pulse, but is brought to zero if no other pacing pulse is applied. These other embodiments are not preferred, however, because they would not result in an exactly balanced charge.

Figure 5:
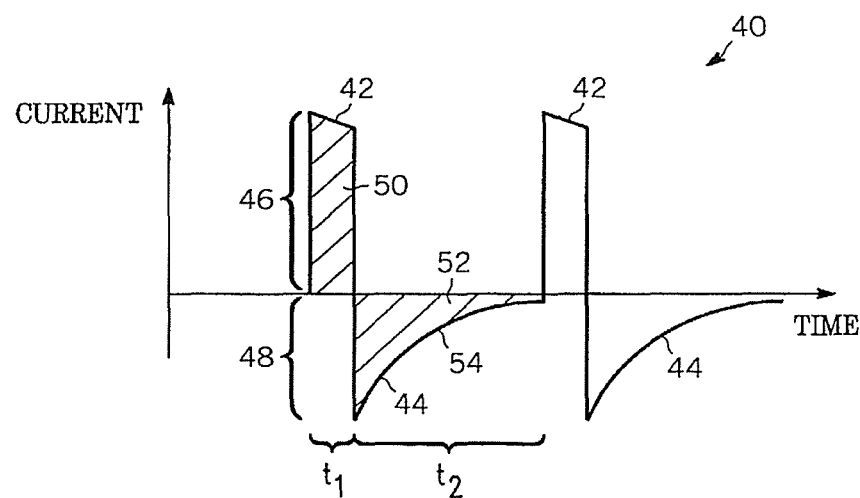
FIG. 5 is a time diagram of a first alternative embodiment of the waveform of FIG. 3 that is preferred for on-demand pacing.

Referring to FIG. 5, an embodiment of the invention is shown where the decay is exponential. A balanced charge waveform 40 includes a positive stimulating pulse 42 and negative compensating pulse 44. The stimulating pulse 42 has an amplitude 46, and a duration t1. The compensating pulse 44 has an initial non-zero amplitude 48, and a duration t2. In the preferred embodiment, area 50 under positive stimulating pulse 42 is balanced by area 52 under compensating pulse 44. The net charge applied to a patient over one period of the balanced charge waveform is thus zero.

Figure 6:
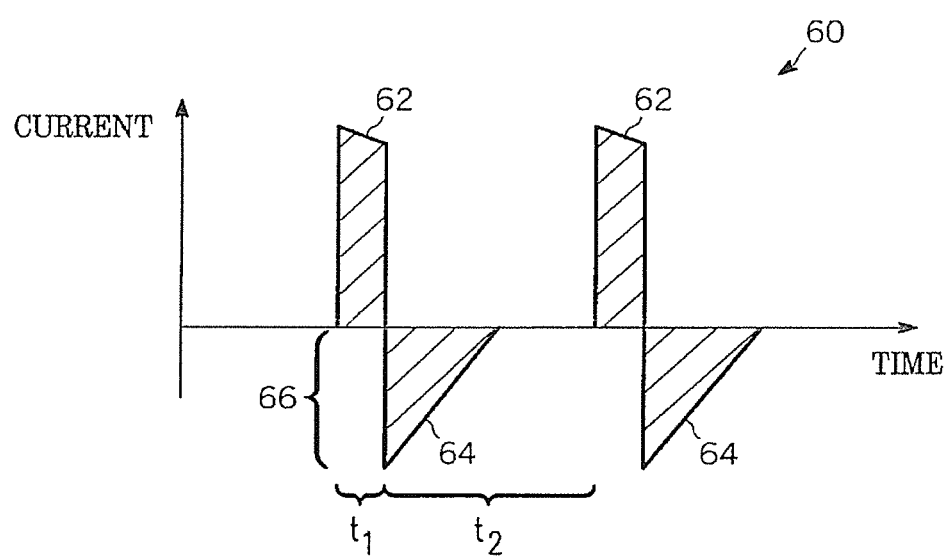
FIG. 6 is a time diagram of a second alternative embodiment of the waveform of FIG. 3 that is preferred for on-demand pacing.

Referring to FIG. 6, an embodiment of the invention is shown where the decay is linear. A balanced charge waveform 60 shown in FIG. 6 consists of a stimulating pulse 62 followed by a compensating current pulse 64 that has an amplitude 66. As in all the balanced charge waveforms disclosed herein, the charge of the stimulating current pulse 62 is equally balanced by the charge of the compensating current pulse 64.

Those skilled in the art will recognize that there are many different forms that the trailing edge of the compensating pulse can take. The two representative forms disclosed herein are advantageous, in that they are easily generated using capacitors as decay elements. Those skilled in the art will recognize, however, that by digitizing the waveforms, the trailing edge can take a variety of different shapes. As disclosed by the method herein, however, two features of the trailing edge are preferably embodied: (1) the amplitude of the compensating current pulse should decay to nearly 0; and (2) the decay is relatively continuous, with few rapid changes in the amplitude, else artifacts might be caused in a monitored heart waveform.

While the preferred embodiment of the invention has been illustrated and described, it will be appreciated that various changes can be made therein without departing from the spirit and scope of the invention. For example, even approximate balancing that only substantially (but not exactly) compensates is within the invention, and will result in substantially alleviating the prior art problems.

What is claimed is:

1. A transcutaneous cardiac pacing method comprising:
applying pacing electrodes to a patient for transcutaneous pacing;
applying through the electrodes a series of cardiac pacing pulses; and
applying through the electrodes a series of compensating pulses interleaved with the cardiac pacing pulses, the compensating pulses having a polarity opposite to a polarity of the cardiac pacing pulses to at least substantially compensate for a charge of the cardiac pacing pulses and configured to:
start approximately immediately at an end of a first cardiac pacing pulse and last up to an onset of a second cardiac pacing pulse that succeeds the first cardiac pacing pulse,
the pacing pulses and compensating pulses being configured so that a net current applied to a patient is substantially or exactly zero.

2. A system for transcutaneous cardiac pacing comprising:
electrodes for transcutaneous pacing;
means for applying through the electrodes a series of cardiac pacing pulses having a first polarity; and
means for applying through the electrodes a series of compensating pulses interleaved with the cardiac pacing pulses, the compensating pulses having a second polarity opposite to the first polarity so that an amount of charge of the second polarity substantially or exactly equal to a charge of the first polarity is applied by the electrodes and configured to:
start approximately immediately at an end of a first cardiac pacing pulse and last up to an onset of a second cardiac pacing pulses that succeeds the first cardiac pacing pulse.

* * * * *